United States Patent
Lehmann

(10) Patent No.: US 7,361,515 B2
(45) Date of Patent: Apr. 22, 2008

(54) METHOD AND TEST KIT FOR DETECTING ANALYTES IN A SAMPLE

(75) Inventor: Werner Lehmann, Lipten (DE)

(73) Assignee: Attomol GmbH Molekulare Diagnostika, Lipten (DE)

( * ) Notice: Subject to any disclaimer, the term of this patent is extended or adjusted under 35 U.S.C. 154(b) by 500 days.

(21) Appl. No.: 10/415,275

(22) PCT Filed: Oct. 23, 2001

(86) PCT No.: PCT/EP01/12364

§ 371 (c)(1), (2), (4) Date: Dec. 9, 2003

(87) PCT Pub. No.: WO02/35228

PCT Pub. Date: May 2, 2002

(65) Prior Publication Data

US 2004/0106215 A1    Jun. 3, 2004

(30) Foreign Application Priority Data

Oct. 27, 2000   (DE) .............................. 100 54 382

(51) Int. Cl.
*G01N 33/543*   (2006.01)

(52) U.S. Cl. .................................................... 436/518

(58) Field of Classification Search ........ 436/514–548, 436/161, 171, 172, 800, 805; 435/4–7.95, 435/283.1–289.1, 973; 356/302, 303, 346, 356/244, 246; 422/50–73

See application file for complete search history.

(56) References Cited

U.S. PATENT DOCUMENTS 4,208,479 A * 6/1980 Zuk et al. ..................... 435/7.9
7,033,754 B2 * 4/2006 Chee et al. ..................... 435/6

* cited by examiner

*Primary Examiner*—Ann Y. Lam
(74) *Attorney, Agent, or Firm*—Millen, White, Zelano & Branigan, P.C.

(57) ABSTRACT

The invention relates to a method and test kit for the detection of analytes in a biological sample, wherein at least one microparticle population is labelled with fluorescent dyes serving as coding fluorescent dyes and reference fluorescent dyes and immobilized, acceptor molecules interacting with labelled analytes being bound to the microparticle population, so that the difference between the fluorescence of the microparticles and analyte(s) can be used to determine which kind of analyte, optionally in which amount, is present in the sample. In particular, the invention finds use in medical diagnostics.

6 Claims, 1 Drawing Sheet

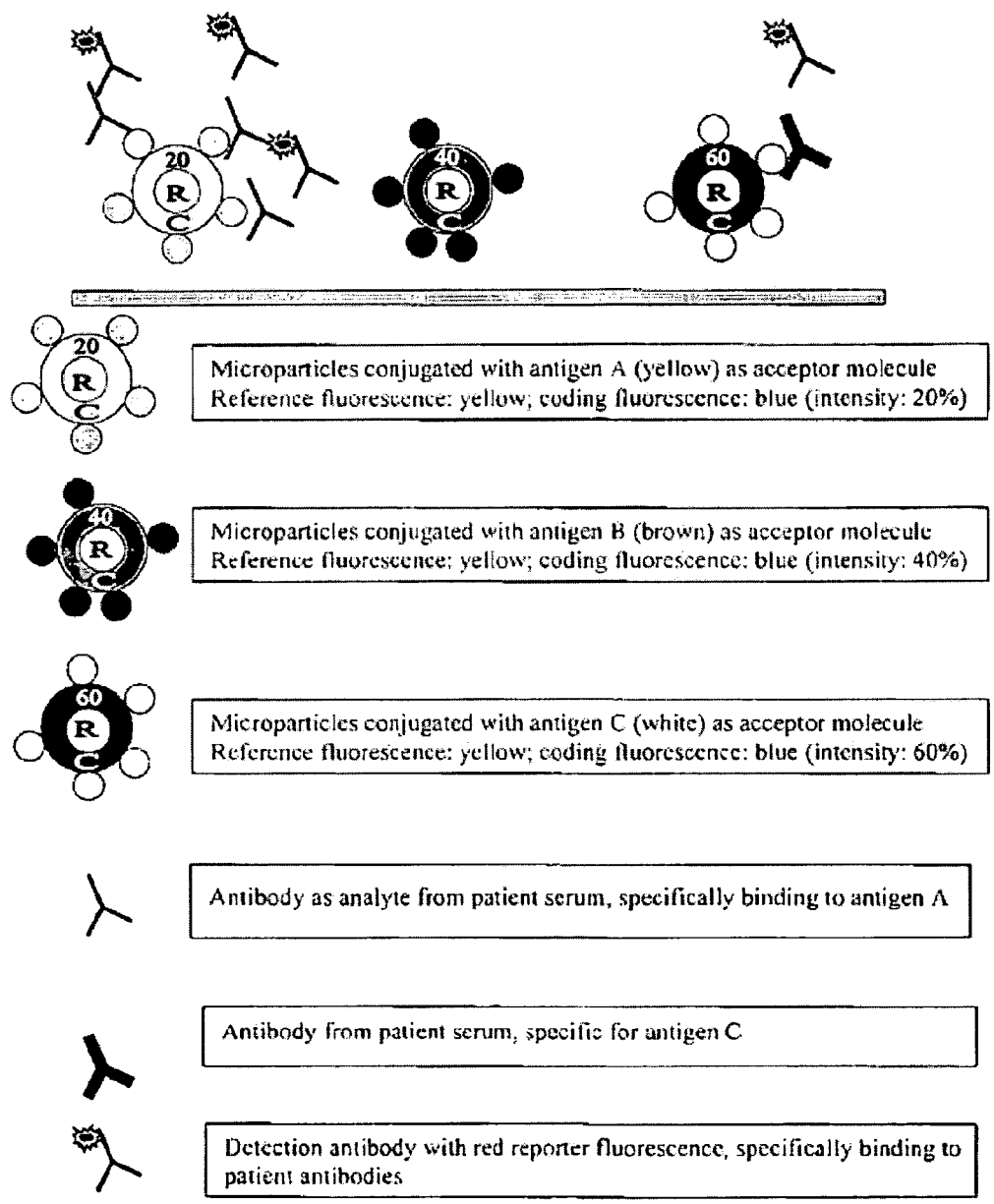

METHOD AND TEST KIT FOR DETECTING ANALYTES IN A SAMPLE

The present invention relates to an efficient and inexpensive method and to a test kit for the detection of analytes in a sample.

In the meaning of the invention, analytes are understood to be chemical and/or biological structures, said biological structures being all those molecules which are formed, taken up or released by organisms; chemical structures are understood to be all those compounds capable of interacting with other molecules in a way so as to allow detection thereof. In the meaning of the invention, a sample is a material collected by sampling, or a portion or small amount thereof, the nature of which is to be investigated by physical, chemical and/or biological means. For example, biological samples are a portion or small quantity of serum, blood, urine, respiratory air, lacrimal fluid, or the like. In addition, however, samples according to the invention are subquantities collected from waste waters, residues from industrial processes, bogs, or from other environmental fluids.

Numerous methods of detecting analytes are known in the prior art. In the field of biological or clinical research and diagnostics, the analytes to be investigated can be proteins, peptides, nucleic acids, sequence fragments, carbohydrates, lipids, and/or antigenic structures, for example.

The informative value of a parameter analysis can be expanded and improved by parallel recording of a larger amount of data from one single sample—the so-called multiparameter analysis or multiligand analysis. Parallel recording also requires miniaturization, for example, by means of which the number of detectable parameters and ligands can be substantially increased. The miniaturized DNA technology allows for analysis of more than $10^6$ parameters per cm$^2$, thus achieving a miniaturization degree of less than 10 µm$^2$/parameter on one chip. Two-dimensional positioning of acceptor molecules—which molecules interact with the ligands—on a chip, e.g. by means of electrolithography or other methods such as piezoelectric printing technology, makes it necessary to repeat for each test kit the positioning procedure on the support material for each acceptor molecule in the same way so as to ensure a regular array on the support.

However, the complex procedures required in electrolithography are suitable only for special fields of use, e.g. in pharmacogenetic investigations.

As an alternative to the methods mentioned above, microparticles as DNA array therefore have also been described in the prior art. Basically, such a microparticle array involves conjugation of multiple suspensions of microparticle populations having different discrete fluorescence labels with respectively specific acceptor molecules (Lackner et al., 1999, Medgen 11, pp. 16-17). Following conjugation of the acceptor molecules, the individual suspensions including the different microparticle populations are mixed, and an aliquot of the mixture is added to the sample solution so that particles of each suspension are present in the reaction batch in mixed state. The ligands in the sample solution which are to be detected will bind to the corresponding acceptor molecules in a ligand-specific fashion and hence, invariably to discrete microparticles of a particular population.

Simultaneously or subsequently, a receptor fluorescence dye is bound to the ligands, the emission wavelength of which is sufficiently different from the emission wavelength of the fluorescent dye used to label the microparticles. The fluorescence used to identify the particles, as well as the reporter fluorescence of ligands bound to the particles is subsequently analyzed in a flow cytometer.

Microparticles which include combinations of fluorescent dyes and can be used in various detection methods are known from the patent documents U.S. Pat. Nos. 5,326,692 and 5,073,498. By combining fluorescent dyes, it is possible to take specific effect on the excitation and emission wavelengths via energy transfer between different dyes incorporated by polymerization. Furthermore, by combining different fluorescent dyes, a more specific definition of microparticle populations in a flow cytometer is possible.

However, a relatively large number of microparticles per sample, about 5,000-10,000 per acceptor (Smith et al., 1998, Clin. Chem. 44, 2054-2056), are required in flow-cytometric measuring methods to allow detection of sufficient microparticles of one population in the measured volume. As a result, the material costs increase, which is particularly disadvantageous in the event of expensive acceptor molecule substances difficult to synthesize.

Another drawback is the relatively low resolution of particle populations when using a flow cytometer. According to Carson et al. (1999, J. Immunol. Methods 227, 41-52), merely 64 particle populations can be individualized when using two fluorescent dyes. Furthermore, Oliver et al. (1998, Clin. Chem. 44, 2057-2060) describe that relatively long measuring periods of about 30 minutes and up to 1 hour per sample are required for specific, parallel and effective detection of multiple parameters. Such long measuring periods sometimes give rise to disadvantageous modification of the ligands and fluorescent dyes.

The invention therefore is based on the object of providing an efficient method and a test kit allowing for shorter measuring periods and higher sensitivity, which are low in cost and can be used in routine operation.

The present invention solves this technical problem by providing a method for the detection of analytes, which method comprises the following steps: fluorescent labelling of at least one microparticle population, said microparticle population comprising at least one fluorescent dye serving as coding fluorescence and at least one fluorescent dye serving as reference fluorescence, binding and/or conjugating acceptor molecules to the microparticle population, immobilizing the microparticle population on a support, incubating the microparticle population with the sample to be investigated, labelling the analyte(s) with at least one fluorescent dye serving as reporter fluorescence, and detecting the analyte(s) by comparing the fluorescence of the microparticle population with the reporter fluorescence.

BRIEF DESCRIPTION OF THE DRAWING

The drawing depicts a scheme illustrating the detection of antibodies in a sample.

The method of the invention comprises several steps which can be modified in terms of their order. For example, it is possible to label the analytes prior to or subsequent to binding to a fluorescent dye serving as reporter fluorescence.

If parallel investigations are to be performed with the method according to the invention, at least two microparticle populations are labelled with fluorescent dyes. Microparticles in the meaning of the invention are heterogeneous and/or homogeneous fractions of microscopic particles having a size of from 1 to 500 µm, particularly from 1 to 100 µm, preferably from 1 to 10 µm. The microparticles may include organic and/or inorganic components. For example, the microparticles can be polymers which, following emulsification or boundary polymerization, precipitate on the material to be entrapped, e.g. on a fluorescent dye. The microparticles may consist of polystyrene or polyphosphoric acid, polyvinyl or polyacrylic acid copolymers. However, it is also envisaged that the microparticles be comprised of oxidic ceramic particles such as silicon dioxide, titanium dioxide or other metal oxides. According to the method of the invention, however, crosslinked polypeptides, proteins, nucleic acids, macromolecules, lipids, e.g. as vesicles and the like, are also microparticles in the meaning of the invention. The preparation of microparticles has been disclosed in the U.S. Pat. Nos. 6,022,564, 5,840,674, 5,788,991, and 5,7543,261, for example.

In the meaning of the invention, a microparticle population is understood to be microparticles resembling each other with respect to labelling with the fluorescent dye or fluorescent dyes. For example, a microparticle population may consist of microparticles labelled with a dye having red, yellow or blue fluorescence and/or with fluorescent dyes with varying lifetime of fluorescence. However, a microparticle population may also be defined by the ratio of different fluorescent dyes. Thus, for example, a microparticle population may include all those microparticles wherein the fluorescent label consists of e.g. green and red fluorescent dyes at a ratio of 1:1. The microparticles of a microparticle population have at least one fluorescent dye serving as coding fluorescence and at least one further fluorescent dye serving as reference fluorescence.

The coding fluorescence serves to analyze the microparticles. The microparticles can be labelled with different fluorescent dyes or with different intensities of the fluorescent dyes. In this way, discrete microparticle populations are formed which can be identified by means of detectors. In addition to the fluorescent dye(s) serving as coding fluorescence, the microparticles include at least one further fluorescent dye serving as reference fluorescence. The reference fluorescence allows for effective referencing of the coding fluorescence. By providing the microparticles with a reference fluorescence and a coding fluorescence, it is possible to correlate the fluorescence signals and compensate for measuring errors in this way.

Fluorescent dyes serving as label of microparticles are all those substances capable of emitting detectable luminescent signals. However, it is also possible to use dyes which emit X rays or exhibit phosphorescence. Fluorescent dyes in the meaning of the invention are all those gaseous, liquid or solid inorganic and/or organic compounds which are characterized in that subsequent to excitation, they emit back the absorbed energy in the form of radiation of equal, longer or shorter wavelength. That is, inorganic or organic luminescent pigments or quantum dots may also be used as fluorescent dyes in the meaning of the invention. However, it is also envisaged that the microparticles be of a nature so as to have autofluorescence or both autofluorescence and a foreign fluorescence label. For example, autofluorescence of the microparticles can be generated by having the microparticles include the mineral fluorite. For example, dansyl chloride, fluorescein isothiocyanate, 7-chloro-4-nitrobenzoxadiazole, pyrenebutyrylacetic anhydride, N-iodoacetyl-N'-(5-sulfo-1-naphthyl)ethylenediamine, 1-anilinonaphthalene-8-sulfonate, 2-toluidinonaphthalene-6-sulfonate, 7-(p-methoxybenzylamino)-4-nitrobenz-2-oxa-1,3-diazole, formycin, 2-aminopurineribonucleoside, ethenoadenosine, benzoadenosine, α- and β-parinaric acid, and/or $\Delta^{9,11,13,15}$-octadecatetraenoic acid, cadmium selenite crystals of one single size or varying sizes and others can be used as foreign fluorescent dyes for a coding and/or reference fluorescence. As fluorescent dyes serving as reference fluorescence, it is possible to use e.g. transition metal complexes containing the following substances: ruthenium(II), rhenium(I) or osmium, and iridium as central atom and diimine ligands; phosphorescent porphyrins with platinum, palladium, lutetium or tin as central atom; phosphorescent complexes of rare earths such as europium, dysprosium or terbium; phosphorescent crystals such as ruby, Cr-YAG, alexandrite, or phosphorescent mixed oxides such as magnesium fluorogermanate or cadmium selenite crystals, fluorescein, aminofluorescein, aminomethylcoumarin, rhodamine, rhodamine 6G, rhodamine B, tetramethylrhodamine, ethidium bromide, and/or acridine orange.

For example, the following substances can be used as fluorescent dyes for the coding fluorescence:

ruthenium(II)-tris(4,7-diphenyl-1,10-phenanthroline)/HPTS
ruthenium(II)-tris(4,7-diphenyl-1,10-phenanthroline)/-fluorescein
ruthenium(II)-tris(4,7-diphenyl-1,10-phenanthroline)/rhodamine B
ruthenium(II)-tris(4,7-diphenyl-1,10-phenanthroline)/rhodamine B octadecyl ester
ruthenium(II)-tris(4,7-diphenyl-1,10-phenanthroline)/hexadecylacridine orange
europium(III)-tris(thionyltrifluoromethyl-acetonate)/hydroxymethylcoumarin
platinum(II)-tetraphenylporphyrin/rhodamine B octadecyl ester
platinum(II)-tetraphenylporphyrin/rhodamine B
platinum(II)-tetraphenylporphyrin/naphthofluorescein
platinum(II)-tetraphenylporphyrin/sulforhodamine 101
platinum(II)-octaethylporphyrin/eosine
platinum(II)-octaethylporphyrin/thionine
platinum(II)-octaethylketoporphyrin/nile blue
Cr(III)-YAG/nile blue and
Cr(III)-YAG/naphthofluorescein
aminocoumarin/aminofluorescein
aminocoumarin/rhodamine 6G
aminocoumarin/tetramethylrhodamine
aminocoumarin/acridine orange
aminofluorescein/rhodamine 6G
aminofluorescein/tetramethylrhodamine
aminofluorescein/ethidium bromide For example, the fluorescent dyes can be incorporated by polymerization during the preparation of the microparticles or subsequently coimmobilized on the microparticles. The fluorescent dyes can be directly introduced in a solvent for the microparticles, e.g. during the preparation of the microparticles. By incorporating the fluorescent dyes by polymerization, precise determination of the amount of fluorescent dyes bound to the microparticles is possible. The fluorescent dyes can be incorporated by polymerization in such a way that the dyes are largely inert or undergo interaction with the analytes. Furthermore, incorporation of the fluorescent dyes in a sol-gel glass as microparticles with subsequent boiling, pulverizing and dispersing of the glass is also possible. When using pulverized fluorescent dyes, the dye can be dispersed in the form of a sensitive layer, e.g. as an exterior coating of the microparticles. For example, this can be done by covalent or electrostatic binding of the fluorescent dyes to the surface of the microparticles. For example, hydroxy groups, amphiphilic electrolytes, phospholipids, and ionic components can be used to bind fluorescent dyes to the surface of microparticles.

According to the invention, the fluorescent-labelled microparticles are intended to conjugate with or bind to acceptor molecules. According to the method of the invention, specific acceptor molecules are coupled to each population of microparticles. The acceptor molecules can be functional groups such as amino groups, carboxyl groups, thiol groups, hydroxyl groups, but also, epitopes, paratopes, carbohydrates, lectins, or oligo- or polynucleotide sequences. For example, epitopes used in immobilization can be antigenic determinants interacting with the antigen-binding portion of an antibody or with a receptor. Paratopes in the meaning of the invention can be e.g. portions of an antibody interacting specifically with antigenic structures. Binding of the acceptor molecules to the respective microparticle population can be covalent, non-covalent, ionic binding or binding by other interactions. According to the invention, the microparticle populations are immobilized on a support. As a result of such immobilization, the microparticles are transferred into a state where reaction space is limited. In the meaning of the invention, immobilization is understood to comprise all those methods resulting in a mobility restriction of the microparticles by biological, chemical or physical means. The supports on which the microparticles are immobilized can be e.g. glass slides, membranes, networks, and/or fibrils. Immobilization of the microparticles on a support may proceed either directly or via spacers. Spacers in the meaning of the invention are all those spacers capable of forming e.g. a short carbon chain between the microparticle and the support. For example, hydroxylated chains can be used in order to avoid specific hydrophobic interactions. However, it is also possible to immobilize the microparticles via the acceptor molecules. When binding the microparticles by means of binding sites of their own, the acceptor molecules can be selected completely at will, because they are not required to mediate binding to a potential support. When immobilizing the microparticles by means of acceptor molecules, the acceptor molecules are intended to have the properties required for this purpose, such as molecular charge, chemically modifiable groups and/or immuno-, nucleic acid or hybridization affinity and the like. When immobilizing the microparticles with the aid of acceptor molecules, immobilization by means of spacers is not necessarily required. Obviously, it might also be envisaged to immobilize the microparticles on the support via binding sites on the surface of the microparticles.

According to the invention, at least one microparticle population is incubated with the sample to be investigated. By incubating the immobilized microparticles and the sample to be investigated, the analytes from the sample can interact with the acceptor molecules bound to the microparticles. If the acceptor molecules are bound antibodies, for example, the analytes—e.g. antigenic structures—can bind thereto. Because the acceptor molecules are bound to the microparticles, binding of the analytes to the microparticles via the acceptor molecules is possible. Advantageously, it is possible to create reaction conditions during incubation of the microparticle population with the sample to be investigated which allow for efficient interaction between the analytes and the microparticle population; such reaction conditions can be elevated temperature, for example. However, it is also possible to agitate or stir the microparticle population in the sample. In particular, the number of microparticle populations immobilized on the support is determined by the number of acceptor molecule specificities required to characterize the analytes. To this end, the desired suspensions e.g. are mixed, and small aliquots of the mixture are pipetted onto the support using a dispenser. The microparticles undergo sedimentation inside the drop, making contact with the surface of the support, thereby allowing binding of 1-1.000.000, particularly 1-100.000, preferably 1-10,000, and more preferably 1-1,000 or less microparticles of a population to the support at random distribution. Drying of the drop on the support is to be prevented particularly in those cases where drying of the acceptor molecules has a disadvantageous effect on the desired binding of the analytes.

According to the invention, labelling of the analytes with at least one reporter fluorescence is envisaged. Obviously, it is possible to label the analytes prior to or subsequent to binding to the acceptor molecules. For example, fluorescein isothiocyanate, tetramethylrhodamine isothiocyanate, Texas red, 7-amino-4-methylcoumarin-3-acetic acid, phycoerythrin and/or cyanins, etc., or antibody-conjugated fluorescent particles binding to the analyte e.g. by means of antibodies can be used as fluorescent molecules. For example, direct labelling of the analytes with a fluorescent dye is possible. By direct labelling of the analytes, it is possible to do without fluorescent-labelled antibodies or other structures carrying labels. In particular, direct labelling of ligands can be performed using fluorescent dyes which emit a fluorescent signal or quench the fluorescence of other labels. However, the analytes can also be enzyme-labelled. Examples of molecules used in enzyme labelling are horseradish peroxidase, alkaline phosphatase and/or glucose oxidase.

According to the method of the invention, detection of the analyte(s) is effected by comparing the fluorescences of the microparticle population with a reporter fluorescence. In a fluorescence spectrometric determination, for example, the fluorescence intensities of the microparticle population and of the analyte(s) can be compared in such a way that, in particular, both the identity of the microparticle population carrying analyte and the number of bound analytes can be analyzed. Hence, it is possible e.g. to provide information as to which analytes are bound to particular discrete microparticle populations and in which number.

It might also be envisaged that the reference fluorescence is not influenced in its parameters by the analytes, while e.g. the intensity of the coding fluorescence may vary depending on the respective concentration of the analytes. Thus, the signal intensity of the microparticle population can be characterized by internal referencing wherein, in particular, an additional excitation source for fluorescence or a second detector to determine the fluorescence is not required. The reference quantity for internal referencing is determined on the basis of the fluorescence intensity and/or time profile of the fluorescence response of the reference fluorescence. Advantageously, the coding fluorescence and reference fluorescence absorb light in the same wavelength region and therefore can be excited with the same excitation source. In this method, the reference fluorescence is not required to exhibit a specific reaction for the molecules to be detected, but provides a constant signal for referencing. However, it is also possible that both the reference fluorescence and coding fluorescence undergo interaction with the analytes. Obviously, it might also be envisaged that neither of reference fluorescence and coding fluorescence interact with the analytes in a way so as to modify the fluorescence signals. According to the invention, the fluorescent dyes for the coding fluorescence and reference fluorescence can be excited simultaneously by a single common source and detected together by a detector. Use of the reference fluorescence to excite the reporter fluorescence may also be envisaged.

In one embodiment of the invention the microparticles are intended to bind to microtest plates, glass slides, flexible membranes, networks or fibrils, particularly those made of polypropylene and/or nitrocellulose, glass and/or polyvinylidene fluoride (PVDF). For example, microtiter plates are used as microtest plates. Advantageously, the microtest plates are dimensioned so as to allow use in numerous laboratory routines. For example, a number of fluorescence measuring instruments, such as fluorescence microscopes and the like, are designed such that microtest plates can be used as standard. Thus, immobilization of the microparticles on special laboratory vessels, e.g. microtiter plates, Petri dishes, multidishes, tray dishes, and other culture vessels and slides, advantageously allows the use of available laboratory means and apparatus for incubation, freezing, lyophilization and of similar laboratory apparatus in clinical or research laboratories. For example, microtiter plates having a transparent, non-fluorescent flat bottom preferably can be used as microtest plates.

In another embodiment of the invention, the intention is to detect a plurality of analytes simultaneously by loading each analyte with individual acceptor molecules via discrete microparticle populations. For example, separate loaded microparticle populations can be labelled and subsequently mixed. Aliquots of the mixture of microparticle populations are then contacted on a support so as to immobilize the microparticles on the support.

Advantageously, the support is subsequently incubated with the sample so that the analytes will bind to the acceptor molecules assigned to the respective microparticle population. Parallel detection of multiple parameters by simultaneous detection of separate analytes allows for characterization of a plurality of analytes with low input of material and time.

However, binding of analytes via a linker molecule may also be envisaged. For example, binding of the linker molecule to the analyte can be covalent or non-covalent. The linker molecule is capable of modulating the mobility of the analytes in such a way that the signal emitted by the analyte or by the fluorescent dye bound to the analyte can be detected efficiently.

In another embodiment of the invention, the analytes are specifically labelled with different fluorescent dyes. The fluorescent dyes may differ in the color of fluorescence, fluorescence lifetime and intensities. Advantageously, a discrete microparticle population can be formed by labelling with fluorescent dyes at varying intensities, which population can be detected in a fluorescence microscope, for example. The number of possible discrete populations particularly depends on the available dyes and techniques of labelling the microparticles and on the number of colors discernable in the detection measuring instrument. Advantageously, about 60 to 100 different discrete microparticle populations can be produced using two colors, for example. By more precise determination of the intensities or by using an additional color, the number of populations can be increased to about 500 to 1000 well-discernable microparticle populations.

In another embodiment of the invention, the analytes are labelled with the same fluorescent dye. Such uniform labelling of the analytes advantageously permits determination of the total number of labelled analytes bound to microparticles. For example, the analytes can be analyzed by assignment to discrete populations using the labels of the microparticles. Preferably, the fluorescent dyes and/or enzymes are present in monomeric and/or polymeric form. For example, the fluorescent dyes can be either inorganic compounds, such as compounds of rare earth metals or uranium compounds, or organic compounds. Instead of labelling by means of fluorescent substrates, it is also possible to use chromogenic substrates, especially those exhibiting chemiluminescence. For sensitive detection of the analytes, binding of fluorescent microparticles to the analytes is also possible.

In a particularly preferred embodiment of the invention, detection of different antibodies in a serologic sample is envisaged (see FIG. 1). Microparticles exhibiting fluorescence in different colors are conjugated with respectively different antigens as acceptors and immobilized on a support via the antigens. During the subsequent incubation, antibodies as analytes from a patient serum advantageously bind to those antigens which are specific therefor. The bound antibodies are detected by means of a secondary antibody having a reporter fluorescence. For assessment, the fluorescence of the microparticles and the reporter fluorescence, especially for each image dot of a microtiter plate cavity, are measured.

The invention also comprises a test kit, said test kit comprising at least one fluorescent-labelled, immobilized microparticle population capable of binding to specific acceptor molecules. According to the invention, the immobilized microparticles comprise at least two fluorescent dyes differing in their spectral properties and/or their lifetime of fluorescence, one dye being used for the coding fluorescence and the other dye for the reference fluorescence. The reference fluorescence is used in referencing the coding fluorescence. Advantageously, the signals of the coding fluorescence can be correlated to the reference fluorescence in the test kit, thereby compensating for measuring errors. For example, the reference fluorescence allows for confident determination as to whether one or more microparticles are located in the measuring area. For example, analytes to be investigated may also have one reporter fluorescence and one reference fluorescence. Advantageously, the ratio of coding fluorescence and reporter fluorescence can be detected more precisely by means of the reference fluorescence. In spite of the low number of microparticles used, the test kit advantageously achieves a measuring accuracy sufficient to meet the requirements of clinical routine, for example. Furthermore, the test kit can be designed in such a way that, owing to the immobilized microparticles, the fluorescence can be evaluated using fluorescence scanners and/or fluorescence microscopes, allowing for e.g. high measuring accuracy and rapidity of the entire process of evaluating the fluorescence, as compared to flow cytometers, for example. The test in the meaning of the invention can be designed in such a way that the microparticles and acceptor molecules—solid or dissolved—are situated in separate reaction vessels, and the fluorescent dyes and reagents for immobilization are also kept separately. To detect an analyte, e.g. immobilization and fluorescent labelling of the microparticle population and binding of the acceptor molecules to the microparticles are effected in such a way that the immobilized and fluorescent-labelled microparticle population with the bound acceptor molecules is present in one single reaction vessel. The sample to be investigated is then placed into this vessel. However, it is also possible to design the test in such a fashion that all of the reagents required to detect the analytes are already present in one single reaction vessel. Advantageously, the test of the invention permits analysis of biological and/or chemical samples. In biological samples such as serum, it is possible to record molecular parameters to characterize complex biomedical conditions, such as immune status or genetic predisposition to specific diseases, or detect the influence on expression. By virtue of such immobilization of a microparticle population, it is possible e.g. to characterize a sample including a small number of analytes to be investigated or of competitive analytes within a very short period of time.

To determine diagnostic serologic parameters, the invention also comprises the use of fluorescent-labelled microparticle populations conjugated with specific acceptor molecules, such as human or animal antibodies against infectious agents, antigens, autoantigens and allergens, pharmacologically significant binding sites in proteoms, genoms and other nucleic acids such as hormone receptors, binding sites of pharmaceuticals, peptides, carbohydrates and DNA, to perform expression analyses of important genes and products thereof, such as tumor proteins, HLA antigens, and to analyze single nucleotide polymorphisms and mutations.

For example, one advantage of the method and test kit of the invention is that immobilization of the microparticle populations allows to reduce the number of particles. Advantageously, this results in a more economical use of the acceptor molecules compared to flow-cytometric methods. The detection of bound analytes via e.g. fluorescent microparticles, quantum dots or luminescent pigments provides a sensitivity down to the region of single molecules. Owing to the 3D structure, especially of porous particles, high and constant acceptor molecule density is achieved, which also contributes to increase the sensitivity and reproducibility. Hence, according to the invention, it is possible to reduce the number of microparticles per sample and the time period of measuring the microparticles, thereby increasing the sensitivity of the measuring procedure. In particular, the use of a reference fluorescence enables particularly easy recognition of measuring areas wherein one single microparticle has been immobilized, which is especially important for automatic evaluation.

By immobilizing the microparticles on standardized supports such as microtiter plates or slides, it is possible e.g. to utilize available laboratory routines such as ELISA autoanalyzing.

Further advantageous embodiments of the invention will be apparent from the description.

Without intending to be limiting, the description will be illustrated with reference to the following example.

EXAMPLE

Detection of Human IgG Antibodies Against Three Microorganisms Pathogenic in Humans Carboxy-modified silica microparticles (sicastar®), 8 µm (micromod), or screenBEADS, 1 µm (chemicell) having the following fluorescent properties are prepared by adding varying amounts of fluorescent dyes to the reaction mixture:
Microparticle population A:
Reference fluorescence: aminocoumarin
Coding fluorescence: 100% aminofluorescein
Microparticle population B:
Reference fluorescence: aminocoumarin
Coding fluorescence: 50% aminofluorescein
Microparticle population C:
Reference fluorescence: aminocoumarin
Coding fluorescence: 0% aminofluorescein Using carbodiimide coupling, bacterial protein mixtures of *Borrelia burgdorferi* are coupled to the microparticle population A, of *Yersinia enterocolitican* to the microparticle population B, and of *Chlamydia trachomatis* to the microparticle population C. To this end,
1. 10 mg of 1-ethyl-3-(3-dimethylaminopropyl)carbodiimide (EDC) is dissolved in 1 ml of distilled water, mixed with 1 ml of bead suspension (25 mg of beads), and incubated for 10 minutes at room temperature;
2. the beads are washed three times with 5 ml of MES buffer, pH 5.0;
3. 500 µg of bacterial protein is dissolved in 1 ml of 0.1 M MES buffer (pH 5.0) and incubated with the activated beads at room temperature with agitation;
4. the beads are washed three times in MES buffer, followed by incubation in MES buffer+0.2 M glycine for 2 hours at room temperature with agitation;
5. the beads are washed three times in PBS, the beads are taken up in 1 ml of PBS, aliquots of 50 µl are produced and frozen at −20° C. for further use.

To immobilize the prepared microparticle populations on the surface of a microtiter plate (format 384, black polystyrene, transparent flat bottom),
1. one aliquot of the particle suspensions of each microparticle population at a time is thawed, mixed and diluted by pipetting 2 µl of each suspension into distilled water so as to make a particle density of 100 microparticles of each population per 1 µl of water;
2. 1 µl of the mixture is pipetted into the center of the cavities of the microtest plate;
3. the microparticles of the three populations employed are immobilized by drying at 45° C.

Thereafter, the cavities are washed three times with PBS+ 0.1% Tween 20 (PBS-T). Human sera at a dilution of 1:100 in PBS-T are then pipetted into the prepared cavities of the microtest plate and incubated for 1 hour at room temperature.

Subsequently, the cavities are washed three times with PBS+0.1% Tween 20 (PBS-T) and incubated for 2 hours at room temperature with goat-antihuman IgG antiserum-phycoerythrin conjugate diluted 1:100 in PBS-T. After washing three times with PBS-T, fluorescence evaluation is effected using an Axiophot fluorescence microscope (Zeiss). The immobilized microparticles are photographed successively with a black-and-white CCD camera using optical filter pairs for the following emission and absorption wavelengths: 390 nm/441 nm, 480 nm/520 nm and 480 nm/578 nm.

Evaluation is effected by data reduction, including only those measuring areas exhibiting a reporter fluorescence intensity above a fixed threshold value. A second data reduction/error compensation is achieved by excluding all those measuring errors from the calculation which are 20% above and 50% below the reference fluorescence. The quotient of the intensities of the coding fluorescence and reference fluorescence provides information as to which microparticle population is concerned. Quotients deviating by more than 10% from the mean of one class result in exclusion of that measuring area from the calculation. For each microparticle population, the reporter fluorescences from 20 measuring areas are divided by the associated reference fluorescences. The resulting quotients from these 20 measuring areas are averaged. They are proportional to the amount of human IgG specifically bound to the bacterial antigens in this microparticle population.

The invention claimed is:
1. A method for determining the presence or amount of analyte(s) in a sample, comprising:
fluorescent labelling of at least one microparticle population, said microparticle population being labelled with at least one fluorescent dye serving as the dye producing a coding fluorescence and at least one fluorescent dye serving as the dye producing a reference fluorescence, binding and/or conjugating acceptor molecules to the microparticle population, immobilizing the microparticle population on a support, incubating the microparticle population with the sample, labelling the analyte(s) with at least one fluorescent dye producing a reporter fluorescence, exciting the fluorescent dyes, determining the presence or amount of analyte(s) in said sample by measuring and comparing the coding fluorescence of the microparticles with the reference fluorescence of the microparticles to identify the microparticle population, and measuring and comparing the reporter fluorescence of analyte(s) with the reference fluorescence of the microparticles to correct for failures caused by varying microparticle sizes within a population.

2. The method according to claim 1, wherein the microparticles are immobilized on microtest plates, glass slides, flexible membranes, networks or fibrils.

3. The method according to claim 1, wherein a plurality of analytes are detected simultaneously by loading each microparticle population with individual acceptor molecules.

4. The method according to claim 1, wherein several analytes are labeled with fluorescent dyes producing reporter fluorescences which are different or identical to each other.

5. The method according to claim 1, wherein microtest plates, flexible membranes, networks, or fibrils which are used as support for immobilizing the microparticle population, are made of at least one of polypropylene, nitrocellulose, glass and PVDF.

6. The method according to claim 1, wherein said sample is a clinical sample or an environmental sample.

* * * * *